United States Patent [19]

Vukovic et al.

[11] Patent Number: 4,778,885
[45] Date of Patent: Oct. 18, 1988

[54] PRODUCTION OF ALKALOID DIMERS USING FERRIC ION

[75] Inventors: John Vukovic, Malton; Anne E. Goodbody, Toronto, both of Canada

[73] Assignee: Allelix Inc., Ontario, Canada

[21] Appl. No.: 908,991

[22] Filed: Sep. 18, 1986

[51] Int. Cl.$^4$ .............................. C07D 519/04
[52] U.S. Cl. .................................... 540/478
[58] Field of Search ......................... 540/478

[56] References Cited

U.S. PATENT DOCUMENTS

| | | | |
|---|---|---|---|
| 3,225,030 | 12/1965 | Svoboda | 540/478 |
| 4,279,817 | 7/1981 | Kutney | 540/478 |
| 4,305,875 | 12/1981 | Potier et al. | 540/478 |

FOREIGN PATENT DOCUMENTS

| | | |
|---|---|---|
| 1094552 | 1/1981 | Canada. |
| 1551054 | 8/1979 | United Kingdom. |

OTHER PUBLICATIONS

Stuart, et al., Heterocycles, vol. 9, No. 10, pp. 1419–1427 (1978).

Synthesis of Bio-Active Substances: Recent Examples, Proceedings of the 7th Workshop Conference, Hoechst, 9/26–27/78, Excerpta Medica, Ansterdam, Oxford, 1979, Potier, pp. 19–27.

Raucher, et al., J. Am. Chem. Soc., vol. 109, No. 2, pp. 442–446 (1987).

Mester, et al., Chemical Abstracts, vol. 101:151184t (1984).

Parasarathy, et al., Chemical Abstracts, vol. 101:210801s (1984).

Khan, et al., J. Indian Chem. Soc., vol. 62(4) 335-7 (1985).

Khan, et al., Chemical Abstracts, vol. 105:133573x (1986) abstract supplied.

*Primary Examiner*—Mark L. Berch
*Assistant Examiner*—Diana G. Rivers
*Attorney, Agent, or Firm*—Wyatt, Gerber, Burke and Badie

[57] ABSTRACT

Alkaloid dimers are formed by coupling vindoline and catharanthine in the presence of ferric ion. The predominant products are 3',4'-anhydrovinblastine and vinblastine when reaction conditions are selected appropriately.

14 Claims, No Drawings

PRODUCTION OF ALKALOID DIMERS USING FERRIC ION

FIELD OF THE INVENTION

This invention relates to alkaloid compounds useful as antitumor agents and as precursors of anti-tumor agents. More specifically, it relates to the preparation of 3',4'-anhydrovinblastine and vinblastine both of which are dimeric indole alkaloids produced naturally by the *Catharanthus roseus* plant.

BACKGROUND OF THE INVENTION

A number of naturally occurring alkaloids found in the Madagascar periwinkle plant *Catharanthus roseus* (also known as *Vinca rosea* and *Lochnera rosea*) are approved anti-tumor drugs. Of prime commercial interest are vincristine and vinblastine which are accepted in the treatment in cancers. Vincristine is an active agent in the treatment of leukemia, lymphomas and solid tumours. Vinblastine has similar activity, and is also an active agent in the treatment of Hodgkin's disease.

Both vinblastine and vincristine are currently obtained by extraction from the plants, which have to be harvested and dried before the drugs can be extracted. The complexity of the plant extract (containing at least 200 different alkaloids) and the low concentrations of the desired alkaloids (0.0003% dry weight for vinblastine) make the extraction process both lengthy and expensive. The problem's inherent in the extraction procedure make the development of alternative methods of vincristine and vinblastine production attractive.

Vincristine can be prepared chemically from vinblastine. In turn, vinblastine can be prepared chemically from catharanthine and vindoline, both natural indole alkaloids found in the *Catharanthus roseus* plant, via an intermediate material, 3',4'-anhydrovinblastine (A-VLB). Catharanthine and vindoline can be chemically coupled using a peracid (e.g. m-chloroperbenzoic acid) to convert catharanthine to its N-oxide, followed by a Polonovski-type fragmentation of the N-oxide initiated with addition of trifluoroacetic acid to form a natural dimer. A reducing agent such as sodium borohydride is then added to the mixture to produce 3',4'-anhydrovinblastine (A-VLB) which can be converted to vinblastine, and thence to vincristine, by further oxidation. The overall chemical reaction scheme can be represented thus:

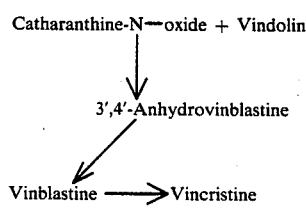

3',4'-anhydrovinblastine (A-VLB), has itself been reported to have a potent cytostatic activity, and indeed shows lower toxicity than either vincristine or vinblastine. It is an essential precursor of vinblastine and vincristine synthesis. Kutney "Pure and Applied Chemistry", 54, 2523 (1982) and "Heterocycles" 9, 1419 (1978) has shown that A-VLB can be formed enzymatically from vindoline and catharanthine using cell-free extracts from *C. roseus* leaves. The yields reported are, however, extremely low.

The chemical coupling reaction of catharanthine and vindoline, in simplified form can be represented as follows:

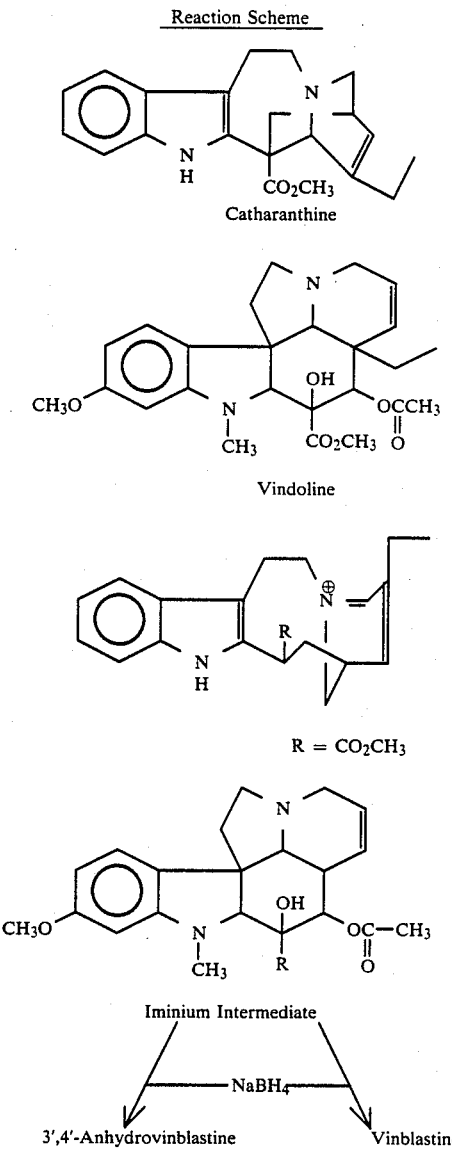

It is an object of the present invention to provide a novel process for coupling catharanthine and vindoline to form dimeric alkaloids.

It is a further object of the present invention to provioe a process for preparing vinblastine and 3',4'-anhydrovinblastine.

SUMMARY OF THE INVENTION

In the present invention, the monomeric alkaloids vindoline and catharanthine are coupled in the presence of a catalytically effective amount of ferric ion. Reaction products include 3',4-anhydrovinblastine and vinblastine as major components. Less significant amounts of catharine and leurosine may also result from the reaction. The extent to which each of the various reaction products is formed can be manipulated to some extent by modifying reaction conditions, discussed in more detail below.

DETAILED DESCRIPTION OF THE PREFERRED EMBODIMENTS

Each of the required reactants is currently available commercially. The monomeric alkaloids vindoline and catharanthine are available in salt form e.g. as vindoline HCl and catharanthine sulfate, and may be used as such in the reaction. Alternatively, the monomers may be extrated from *C. roseus* tissue by methods described in the art: see for example U.S. Pat. No. 1.094,552 issued Jan. 27, 1981.

The source of the ferric ion may vary provided that the ferric ion is released in the reaction medium and is therefore made available to participate in the reaction. Compounds in which the ferric ion is chelated strongly, such as the $Fe^{3+}$:EDTA complex and ferric pyrophosphate, should be avoided. More suitable $Fe^{3+}$ sources include the sulfate, ammonium sulfate, monophosphate, chloride and nitrate salts.

The reaction is conducted simply by adding a catalytically effective amount of ferric ion to a reaction medium containing vindoline and catharanthine. While the reaction will proceed in unbuffered, aqueous medium at room temperature, it is desirable to control reaction progress to maximize production of the desired dimeric alkaloids. For example, the reaction is able to proceed by forming A-VLB and vinblastine initially. Continued oxidation of these dimerics will result in other products such as vinblastine, catharine, leurosine, vinamidine and 3-R-hydroxyvinamidine, the relative amounts depending upon reaction conditions. Accordingly, A-VLB and vinblastine production can be optimized to limit formation of other dimers and maximize yields. To this end, such factors as pH, reaction temperature, ferric ion concentration, reaction medium and reaction time may be manipulated with a view particularly to producing A-VLB and/or vinblastine in economically significant yields, given their desirable pharmaceutical utilities.

The reaction medium can be selected from a variety of solvents. Aqueous medium may be used. While water per se may be used, dilute aqueous mineral acids such as HCl, $H_2SO_4$, $HNO_3$, $H_3PO_4$ and the like are equally useful and, in fact, are preferred in some instances since they contribute to the ability to control reaction rates. Aqueous organic acids such as acetic acid may also be employed. In addition, water miscible, aprotic solvents such as dimethylformamide and tetrahydrofuran may be employed, if desired. Further, a solvent system may be used which assists in driving the reaction toward product formation. Such a solvent system will permit the dimeric products to separate from catalyst as the dimerics form. Suitable systems may include two-phase solvent systems comprising a hydrophobic component such as methylene chloride, carbon tetrachloride, chloroform and other halogenated lower hydrocarbons, ethyl acetate and ethers such as diethyl ether or the like and a hydrophilic i.e. water miscible component such as the aqueous solvents described above. By continued agitation of the solvent mixture, the dimeric products are encouraged into the hydrophobic phase from which they may be extracted by known techniques. The catalyst may be recovered from the aqueous phase, if desired.

The pH at which the reaction should be conducted will vary, depending on the product desired. The pH has a notable effect on the type of product formed and can be controlled directly when aqueous mineral acids and/or organic acids constitute the reaction medium simply by monitoring pH during acid addition or by quantitatively determining required acid strength or volume prior to initiation of the reaction by $Fe^{3+}$ addition. Where water is used as the solvent, the reaction medium may be suitably buffered, such as by glycine, to maintain a desired pH range. It should be borne in mind that addition of $Fe^{3+}$ to the medium will, per se, lower the pH of the medium, the resulting pH reflecting the final concentrations of $Fe^{3+}$ in the medium.

Under the conditions most preferred herein, A-VLB production is at a maximum at around pH 1.50 and lower. Higher pH, say between pH 1.50 and 4, evidently enhances relative vinblastine yield than at the lower pH levels although A-VLB is still the predominant dimer in the reaction products. These lower pH ranges reflect the relative yields of A-VLB and vinblastine as observed at 4° C. but are not necessarily to be adhered to rigidly.

The temperature at which the reaction should be conducted can vary over a wide range. Since temperature is an effective means of controlling reaction rate, it is a parameter by which formation of reaction products is preferably manipulated. At higher temperatures, e.g. from room temperature to about 40° C., the reaction proceeds very quickly, requiring precisely timed addition of a reducing agent to halt reaction progress when the presence of the desired dimer is at a maximum. Further, high temperatures usually involve increased reactivity with atmospheric oxygen which can oxidize A-VLB and vinblastine to undesired dimers. Accordingly, when A-VLB and vinblastine are desired and the reaction is conducted at higher temperatures, the reactants should be exposed to an inert atmosphere, e.g. $N_2$, to provide for better control over the type of product formed. Oxygen scrubbing may be performed.

By conducting the reaction at colder temperatures, the reaction rate is controlled more effectively and the exact timing of addition of reducing agent to halt the reaction becomes more flexible. Reaction at 10° C. and lower, e.g. 4° C., reduces the rate of oxidation of A-VLB and vinblastine so that the need to operate in inert atmosphere can be eliminated for practical purposes. Glycine buffer appears to provide for the enhanced production of vinblastine at these lower temperatures and its use is therefore preferred where a buffer is employed at low temperatures. Other buffers may be used such as phosphate, Tris and the like but care should be taken to select a buffer which does not bind the ferric ion.

Reaction progress is also dependent upon the concentration of ferric ion in the medium. Preferred catalytically effective amounts of ferric ion, assessed as final concentrations, range from 1 to $10^4$ moles $Fe^{3+}$ per mole catharanthine. More preferred final concentrations of $Fe^{3+}$ range from 400:1 to 1,000:1. The reference in the molar ratio to catharanthine reflects what is presently theorized to be the reaction mechanism. It is presumed that the ferric ion complexes with catharanthine, causing an electron shift which promotes appropriate coupling to vindoline. Accordingly, the $Fe^{3+}$ concentration, together with the relative catharanthine concentration is likely the initial controlling factor in the reaction.

Regardless of the reaction conditions selected, the reaction progress should be halted by addition of a reducing agent such as sodium borohydride at a time when the desired dimer is at its peak concentration. Earlier addition of the reducing agent will prevent recovery of the dimer, A-VLB or vinblastine, in maximum yield. Later addition of the reducing agent will allow the reaction to proceed beyond the stage at which A-VLB predominates and at which vinblastine formation is at a maximum. The interval within which the reducing agent is added will vary depending on reaction conditions, ferric ion concentration, etc. As an example, using 100 mM ferric chloride as ferric ion source to initiate coupling of 0.5 mg each of catharanthine and vindoline in aqueous HCl at 4° C., maximum A-VLB yield is obtained after three hours. Using 20 mM $FeCl_3$ in unbuffered aqueous medium but with otherwise similar conditions, maximum A-VLB is realized after about four hours. Maximum vinblastine yields were realized when the reaction of 0.5 mg each of vindoline and catharanthine conducted in glycine buffer containing 40 mM ferric chloride, was halted after two hours. Thus, it may be necessary to analyze a reaction quantitatively prior to upscaling, in order to determine the appropriate interval in the progress of the reaction for adding the reducing agent. Tests such as those outlined in the following examples are suitable although the design of similar such experiments are well within the purview of the skilled artisan.

Once the reaction is stopped, the dimers may be extracted into polar organics, such as ethyl acetate and purified using standard chemical techniques.

Embodiments of the present invention are exemplified hereinafter. For each of the examples, the presence of vinblastine and A-VLB was confirmed by mass spectral analysis, circular dichroism analysis and UV spectra. UV spectra was consistent to the first order derivative by comparison with known standards. Circular dichroism confirmed α-coupling about the C-18'carbon.

EXAMPLE 1

Fresh samples containing 0.5 mg of catharanthine (as sulfate salt) and 0.5 mg of vindoline (as HCl salt) in 0.1 M glycine buffer (pH 2.0 at 4C) were precooled to 4C. To these mixtures were added varying amounts of an aqueous stock solution of either 1.2M ferric chloride or 0.6M ferric sulfate resulting in concentrations of ferric ion that ranged from 20 mM to 100 mM in a final sample volume of 6.0 ml. After initiation of the reaction with the ferric moeity, the samples were shaken at 4C and quenched at 0.5, 1 and 2 hours of incubation through the addition of a molar excess amount of sodium borohydride and 1.0 ml of 14M aqueous ammonium hydroxide. The results are tabulated in Tables 1 and 2 below.

TABLE 1

| | $FeCl_3$ as $Fe^{3+}$ Source | | |
|---|---|---|---|
| $[Fe^{3+}]$ (mM) | Time (hours) | A-VLB yield (%) | VLB yield (%) |
| 20 | 0.5 | 15.04 | 15.37 |
| | 1.0 | 29.615 | 15.01 |
| | 2.0 | 34.75 | 18.44 |
| 40 | 0.5 | 11.005 | 19.43 |
| | 1.0 | 37.455 | 17.33 |
| | 2.0 | 41.44 | 21.34 |
| 60 | 0.5 | 9.72 | 19.80 |
| | 1.0 | 35.86 | 20.80 |
| | 2.0 | 42.58 | 20.66 |
| 80 | 0.5 | 15.77 | 17.39 |
| | 1.0 | 36.595 | 19.32 |
| | 2.0 | 37.315 | 18.88 |
| 100 | 0.5 | 20.84 | 18.725 |
| | 1.0 | 59.11 | 15.24 |
| | 2.0 | 40.43 | 17.54 |

TABLE 2

| | $Fe_2(SO_4)_3$ as $Fe^{3+}$ Source | | |
|---|---|---|---|
| $[Fe^{3+}]$ (mM) | Time (hours) | A-VLB yield (%) | VLB yield (%) |
| 20 | 0.5 | 15.10 | 14.62 |
| | 1.0 | 25.775 | 17.265 |
| | 2.0 | 34.895 | 19.70 |
| 40 | 0.5 | 27.02 | 16.23 |
| | 1.0 | 44.67 | 13.03 |
| | 2.0 | 44.17 | 19.23 |
| 60 | 0.5 | 32.18 | 19.07 |
| | 1.0 | 45.20 | 16.72 |
| | 2.0 | 48.23 | 19.40 |
| 80 | 0.5 | 41.14 | 18.15 |
| | 1.0 | 52.205 | 16.24 |
| | 2.0 | 51.50 | 17.78 |
| 100 | 0.5 | 50.355 | 15.22 |
| | 1.0 | 58.495 | 15.14 |
| | 2.0 | 57.89 | 16.35 |

Dimeric alalkoids produced in the reaction were analysed by extracting the samples three times with 6.0 ml of ethyl acetate (HPLC-grade). The organic fractions were pooled, dried in vacuo and reconstituted with 200 ul of HPLC-grade methanol. HPLC analysis of the samples was performed on a C-8, 5 μm column with UV spectral analysis of observed peaks of interest corresponding to 3', 4'-anhydrovinblastine, vinblastine, leurosine and catharine, respectively. TLC analysis on silica-coated plates developed at ambient temperature with ether:chloroform:methanol (50:35:20) containing 0.5 %(v/v) triethylamine was performed. Both UV spectra generated and development of the alkaloids with ceric ammonium sulfate, corroborated the presence of the aforementioned dimerics.

It will be apparent from Tables 1 and 2 that, yields as high as 21.34% (weight %) for vinblastine (40 mM ferric chloride; t=2 hours) and 59.11% (weight %) for 3',4-anhydrovinblastine (100 mM ferric chloride; t=1 hour) were realized.

EXAMPLE 2

Samples containing 0.5 mg catharanthine (as sulfate salt) and 0.5 mg vindoline (as HCl salt) were suspended in aqueous hydrochloric acid ranging in concentration from 0.001 to 0.05 Molar and cooled to 4C. Chemical coupling of the monomers was initiated upon the addition of a stock 1.2M ferric chloride solution to final ferric levels of 20 to 100mM in a total volume of 6.0 ml. Samples were shaken at 4C and quenched at 0.5, 1, 2 and 3 hours of incubation through the addition of molar excess amounts of sodium borohydride and 1.0 ml of 14M aqueous ammonium hydroxide. The results are tabulated in Table 3 below.

TABLE 3

| [HCl] (N) | $[Fe^{3+}]$ (nM) | pH* | Time (hours) | A-VLB yield (%) | VLB yield (%) |
|---|---|---|---|---|---|
| 0.001 | 20 | 2.19 | 0.5 | 22.495 | 0.94 |
| | | | 1.0 | 27.65 | 2.395 |
| | | | 2.0 | 25.465 | 3.86 |
| | | | 3.8 | 29.285 | 2.11 |
| | 40 | 2.04 | 0.5 | 27.795 | 4.695 |
| | | | 1.0 | 28.745 | 4.265 |

TABLE 3-continued

| [HCl] (N) | [Fe$^{3+}$] (nM) | pH* | Time (hours) | A-VLB yield (%) | VLB yield (%) |
|---|---|---|---|---|---|
| | | | 2.0 | 46.385 | 7.22 |
| | | | 3.0 | 34.81 | 1.905 |
| | 60 | 1.95 | 0.5 | 17.685 | 3.42 |
| | | | 1.0 | 16.60 | 5.115 |
| | | | 2.0 | 37.39 | 9.31 |
| | | | 3.0 | 37.815 | 4.065 |
| | 80 | 1.85 | 0.5 | 17.255 | 2.115 |
| | | | 1.0 | 16.66 | 4.525 |
| | | | 2.0 | 39.08 | 11.145 |
| | | | 3.0 | 36.76 | 3.52 |
| | 100 | 1.76 | 0.5 | 13.31 | 3.79 |
| | | | 1.0 | 16.745 | 4.83 |
| | | | 2.0 | 40.20 | 8.455 |
| | | | 3.0 | 39.45 | 5.145 |
| 0.005 | 20 | 1.96 | 0.5 | 24.615 | 5.205 |
| | | | 1.0 | 35.66 | 3.42 |
| | | | 2.0 | 29.78 | 1.485 |
| | | | 3.0 | 31.45 | 4.245 |
| | 40 | 1.74 | 0.5 | 38.695 | 8.36 |
| | | | 1.0 | 40.915 | 4.645 |
| | | | 2.0 | 50.605 | 2.40 |
| | | | 3.0 | 23.60 | 6.495 |
| | 60 | 1.74 | 0.5 | 49.415 | 10.815 |
| | | | 1.0 | 46.71 | 6.205 |
| | | | 2.0 | 47.06 | 2.83 |
| | | | 3.0 | 36.725 | 6.255 |
| | 80 | 1.70 | 0.5 | 55.215 | 11.665 |
| | | | 1.0 | 41.105 | 6.60 |
| | | | 2.0 | 18.925 | 5.16 |
| | | | 3.0 | 37.69 | 5.83 |
| | 100 | 1.64 | 0.5 | 48.12 | 9.45 |
| | | | 1.0 | 24.76 | 8.53 |
| | | | 2.0 | 37.03 | 3.985 |
| | | | 3.0 | 28.80 | 6.14 |
| 0.01 | 20 | 2.00 | 0.5 | 39.0 | 1.535 |
| | | | 1.0 | 45.465 | N.A. |
| | | | 2.0 | 31.97 | 1.07 |
| | | | 3.0 | 44.317 | 3.125 |
| | 40 | 1.82 | 0.5 | 40.335 | 5.72 |
| | | | 1.0 | 32.845 | 4.815 |
| | | | 2.0 | 35.785 | 2.27 |
| | | | 3.0 | 40.375 | 6.91 |
| | 60 | 1.79 | 0.5 | 47.935 | 3.88 |
| | | | 1.0 | 30.02 | 5.845 |
| | | | 2.0 | 30.485 | 3.295 |
| | | | 3.0 | 40.18 | 7.235 |
| | 80 | 1.72 | 0.5 | 42.965 | 5.635 |
| | | | 1.0 | 34.42 | 8.19 |
| | | | 2.0 | 36.21 | 3.58 |
| | | | 3.0 | 42.355 | 9.135 |
| | 100 | 1.63 | 0.5 | 36.54 | 6.535 |
| | | | 1.0 | 38.815 | 6.37 |
| | | | 2.0 | 41.70 | 3.32 |
| | | | 3.0 | 46.52 | 6.89 |
| 0.05 | 20 | 1.65 | 0.5 | 13.185 | 0.995 |
| | | | 1.0 | 10.785 | 2.145 |
| | | | 2.0 | 24.04 | 0.925 |
| | | | 3.0 | 62.865 | 3.455 |
| | 40 | 1.57 | 0.5 | 32.73 | 1.53 |
| | | | 1.0 | 20.53 | 3.52 |
| | | | 2.0 | 32.87 | 2.66 |
| | | | 3.0 | 49.665 | 7.84 |
| | 60 | 1.50 | 0.5 | 23.785 | 4.13 |
| | | | 1.0 | 44.47 | 5.87 |
| | | | 2.0 | 29.30 | 4.56 |
| | | | 3.0 | 45.825 | 11.41 |
| | 80 | 1.45 | 0.5 | 44.635 | 6.135 |
| | | | 1.0 | 37.90 | 6.395 |
| | | | 2.0 | 35.90 | 3.81 |
| | | | 3.0 | 53.045 | 10.085 |
| | 100 | 1.41 | 0.5 | 36.77 | 8.34 |
| | | | 1.0 | 38.24 | 7.475 |
| | | | 2.0 | 33.765 | 5.21 |
| | | | 3.0 | 68.63 | 12.33 |

*pH of sample recorded prior to termination of reaction.

Quenched samples were extracted three times with 6.0 ml of ethyl acetate (HPLC-grade) and the pooled organic fraction dried in vacuo. Sample reconstituted with 200 μl of HPLC-grade metahnol were subjected to HPLC and TLC analyses.

HPLC analysis on a C-8, 5 μm column consisted of a complex gradient running from 55 to 90% methanol in water containing t-butyl ammonium phosphate as modifier. UV spectral scanning of peaks exhibiting similar retention times to known standard dimerics confirmed the presence of 3′, 4′-anhydrovinblastine, vinblastine, catharine and leurosine. TLC on silica-coated plates developed in toluene:acetone:methanol:ammonium hydroxide(aqueous,14M) (28:10:3:0.5 ) followed by UV spectral analysis and ceric ammonium sulfate treatment of spots co-migrating with known standards further corroborates the presence of the aforementioned dimerics.

Following the above procedure, best values of 12.33% (weight %) for vinblastine and 68.63% (weight %) for 3′,4′-anhydrovinblastine were observed at 100 mM ferric chloride in 0.5M hydrochloric acid after 3 hours of incubation.

EXAMPLE 3

Reaction mixtures containing 0.5 mg catharanthine (as sulfate salt) and 0.5 mg vindoline (as HCl salt) were prepared in 0.005N aqueous mineral/organic acids and cooled to 4C. Dimer production was initiated through the addition of ferric chloride to a final concentration of 80 mM in a final sample volume of 6.0 ml. Acids assayed included: acetic, hydrochloric, nitric, phosphoric and sulphuric. The results appear in Table 4 below.

TABLE 4

| Acid | time (hours) | A-VLB yield (%) | VLB yield (%) |
|---|---|---|---|
| Acetic | 0.5 | 37.71 | 0.67 |
| | 1.0 | 51.60 | 1.065 |
| | 2.0 | 52.03 | 2.79 |
| HCl | 0.5 | 42.21 | 0.15 |
| | 1.0 | 66.64 | 2.93 |
| | 2.0 | 67.10 | 2.245 |
| HNO$_3$ | 0.5 | 42.65 | 0.53 |
| | 1.0 | 67.05 | 1.11 |
| | 2.0 | 58.10 | 1.56 |
| H$_3$PO$_4$ | 0.5 | 43.03 | 1.005 |
| | 1.0 | 61.26 | 0.795 |
| | 2.0 | 49.76 | 2.705 |
| H$_2$SO$_4$ | 0.5 | 43.37 | 1.05 |
| | 1.0 | 57.84 | 1.835 |
| | 2.0 | 47.98 | 3.24 |

After incubation times of 0.5, 1 and 2 hours, with shaking at 4C, the samples were quenched with molar excess sodium borohydride and 1.0 ml of 14M aqueous ammonium hydroxide. Quenched samples were further processed by extracting three times with ethyl acetate (HDLC-grade). Organic fractions were pooled, dried in vacuo and the residue reconstituted with 200 μl of HPLC-grade methanol.

Analysis of the samples by HPLC on a C-8, 5μm column and associated spectral evidence suggested the presence of the dimerics; 3′, 4′-anhydrovinblastine, vinblastine, catharine and leurosine. TLC on silica-coated plates developed in toluene:acetone:methanol:ammonium hydroxide(14M, aqueous) (28:10:3:0.5) and subsequent UV spectral determinations as well as ceric ammonium sulfate treatment of spots co-migrating with known stancards further substantiated the presence of the aforementioned dimerics.

Utilizing the described regimen, values of 3.24% (weight %) for vinblastine (0.005M sulfuric acid; t=2 hours) and 67.10% (weight %) for 3',4'-anhydrovinblastine (0.005M HCl; t - 2 hours) were achieved.

EXAMPLE 4

Unbuffered aqueous reaction mixtures containing 0.5 mg catharanthine (as sulfate salt) and 0.5 mg vindoline (as HCl salt) were incubated at 4C with shaking. Coupling of the monomers was initiated through the addition of ferric chloride to a final concentration of 20 mM in a total sample volume of 6.0 ml. Samples were quenched at 1, 2, 3 and 4 hours of incubation with molar excess amounts of sodium borohydride and 1.0 ml of 14M aqueous ammonium hydroxide. Quenched samples were further processed through organic extraction, three times, with 6.0 ml of ethyl acetate (HPLC-grade). Organic fractions were pooled, dried in vacuo and the residue reconstituted in 200 ul of HPLC-grade methanol.

The presence of the dimeric indole alkaloids (3',4'-anhydrovinblastine, vinblastine, catharine and leurosine) were ascertained through a combination of both HPLC, on a C-8, 5μm column, and TLC on silica-coated plates developed in toluene:acetone:methanol:ammonium hydroxide(14M, aqueous) (28:10:3:0.5 ). UV spectral analyses in both of these systems, in comparison with known standards, confirmed the presence of the aforementioned dimerics. The results are given in Table 5, below.

TABLE 5

| Time (hours) | A-VLB yield (%) | VLB yield (%) |
| --- | --- | --- |
| 1.0 | 26.665 | 3.68 |
| 2.0 | 26.715 | 3.14 |
| 3.0 | 35.915 | 6.175 |
| 4.0 | 42.20 | 4.685 |

With the above procedure, best values obtained were 6.18% (weight %) for vinblastine (t=3 hours) and 42.2% (weight %) for 3',4'-anhydrovinblastine (t=4 hours).

EXAMPLE 5

Aqueous solutions containing 0.5 mg each of vindoline and catharanthine were added to 0.1M glycine buffer of pH's 2.0, 2.5 and 3.0 containing 20 mM ferric ion in a final volume of 6.0 ml.

After incubation at 30° C. for 1 hour with intermittent agitation, the reaction was terminated through the addition of a molar excess amount of sodium borohydride and 0.2 ml of 14M aqueous ammonium hydroxide.

Organic extraction of the samples was performed three times with ethyl acetate (HPLC-grade), the extracts pooled, dried in vacuo and reconstituted with 0.2 ml of HPLC-grade methanol.

HPLC analysis of the samples on a C-8, 5um column led to the findings summarized in Table 6. UV spectral analysis of peaks co-eluting with known standards verified the presence of the dimerics of interest.

TABLE 6

| Buffer pH | Sample pH* | % AVLB | % VLB |
| --- | --- | --- | --- |
| 2.0 | 1.91 | 22.45 | N.D.** |
| 2.5 | 2.26 | 27.28 | N.D. |
| 3.0 | 2.70 | 14.80 | N.D. |

*pH of sample prior to quenching
**N.D. = Below limits of detection

As evidenced by the values of Table 6, 0.1M glycine (pH=2.5) appears best for AVLB production (27.28%, yield by weight) under these conditions.

Thus, the reactions described herein are suited to qeneration of 3',4'-anhydrovinblastine and vinblastine. Manipulations of reaction conditions can lead to preferential formation of either A-VLB or vinblastine.

While reaction conditions may include cold temperatures and complex aqueous solutions, it is acnowledged that commercial operations are conducted more preferably at room temperature etc., i.e. using inexpensive reaction conditions. The present invention encompasses such process conditions as room temperature, use of unbuffered water as solvent and the like. Under such conditions, however, an inert atmosphere is desirable. Further, the reaction rate should be controlled, if necessary, by manipulating ferric ion addition. At these higher temperatures, ferric ion concentration can be reduced.

What is claimed is:

1. A process for producing a mixture of dimeric alkloids comprised principally of 3'-4'-anhydrovinblastine and vinblastine which comprises reacting vindoline and catharanthine in an aqueous medium in the presence of an effective amount of ferric ion.

2. The process according to claim 1 wherein the ferric ion is present in the medium in a molar ratio with respect to catharanthin of from 1:1 to 10,000:1.

3. The process according to claim 2 wherein the molar ratio is from 400:1 to 1,000:1.

4. A process as in claim 1 or 2 conducted at ambient temperature further characterized in that the reaction is quenched by the addition of a reducing agent, and at least one of the dimeric alkaloids produced is recovered from the reaction medium.

5. A process as in claim 1 or 2 conducted at a temperature up to 10° C. and a pH up to about 1.5 whereby the amount of 3',4'-anhydrovinblastine produced is increased compared to the amount produced when the reaction is conducted at a higher pH.

6. A process as in claim 1 or 2 conducted at a temperature up to 10° C. and a pH from 1.5 to 4 whereby the amount of vinblastine produced is increased compared to the amount produced when the reaction is conducted at a lower pH.

7. A process as in claim 1 or 2 conducted at a temperature up to 10° C. and a pH up to about 1.5 whereby the amount of 3', 4'-anydydrovinblastine produced is increased compared to the amount produced when the reaction is conducted at a higher pH, further characterized in that the reaction is quenched by the addition of a reducing agent, and the 3',4'-anhydrovinblastine is recovered.

8. A process as in claim 1 or 2 conducted at a temperature up to 10° C. and a pH from 1.5 to 4 whereby the amount of vinblastine produced is increased compared to the amount produced when the reaction is conducted at a lower pH and the vinblastine is recovered.

9. A process as in claim 1 conducted at a temperature up to 40? C.

10. 1 A process as in claim 9 conducted in an inert atmosphere.

11. A process as in claim 9 wherein the ferric ion is present in the medium in a molar ratio with respect to catharanthine of from 1:1 to 10,000:1.

12. A process as in claim 11 wherein the molar ratio is from 400:1 to 1,000:1.

13. A process as in claim 10 wherein the ferric ion is present in the medium in a molar ratio with respect to catharanthine of from 1:1 to 10,000:1.

14. A process as in claim 13 wherein the molar ratio is from 400:1 to 1,000:1.

* * * * *